United States Patent [19]

Baker et al.

[11] 3,966,809

[45] June 29, 1976

[54] INSECT REPELLENT COMPOUNDS

[75] Inventors: Don R. Baker, Orinda; Francis H. Walker, Mill Valley; Peter E. Letchworth, Cupertino, all of Calif.

[73] Assignee: Stauffer Chemical Company, Westport, Conn.

[22] Filed: Dec. 24, 1974

[21] Appl. No.: 536,277

Related U.S. Application Data

[62] Division of Ser. No. 417,306, Nov. 19, 1973, abandoned.

[52] U.S. Cl. ............... 260/559 R; 260/239 B; 260/293.77; 260/295 AM; 260/326.4; 260/347.3; 260/558 R; 424/244; 424/256; 424/274; 424/324

[51] Int. Cl.² ........................................ C07C 103/75

[58] Field of Search ............ 260/558 R, 559 R, 558, 260/559

[56]  References Cited
UNITED STATES PATENTS

| | | | |
|---|---|---|---|
| 3,187,042 | 6/1965 | Richter | 260/558 R |
| 3,436,208 | 4/1969 | Lemin | 71/118 |
| 3,551,484 | 12/1970 | Lewis et al. | 260/558 R |
| 3,825,594 | 7/1974 | Houlihan | 260/558 R |
| 3,835,189 | 9/1974 | Arsura et al. | 260/558 R |

OTHER PUBLICATIONS
Johnson et al., J. Econ. Entol. 60 (1967) pp. 173–176.

*Primary Examiner*—Arthur P. Demers
*Attorney, Agent, or Firm*—Edith A. Rice; Daniel C. Block

[57] ABSTRACT

This application is directed to novel compounds useful as insect repellents. The compounds of this invention have the following generic formula:

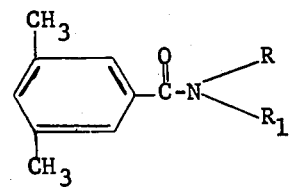

wherein R is selected from the group consisting of hydrogen, alkyl, alkoxyalkyl, alkenyl, and cyanoalkyl; $R_1$ is selected from the group consisting of alkyl, alkenyl, haloalkenyl, cycloalkenyl, alkoxyalkyl, and furfuryl; R and $R_1$ taken together can form a ring structure selected from alkylene, alkyl substituted alkylene, alkenylene and alkyl substituted alkenylene.

6 Claims, No Drawings

INSECT REPELLENT COMPOUNDS

This is a division of application Ser. No. 417,306 filed Nov. 19, 1973, now abandoned.

DESCRIPTION OF THE INVENTION

The compounds of this invention may be generally described as dimethyl substituted aryl amides that are useful as insect repellents. The compounds of this invention have the following generic formula:

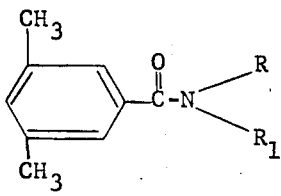

wherein R is selected from the group consisting of hydrogen, alkyl, alkoxyalkyl, alkenyl, and cyanoalkyl; $R_1$ is selected from the group consisting of alkyl, alkenyl, haloalkenyl, cycloalkenyl, alkoxyalkyl, and furfuryl; R and $R_1$ taken together can form a ring structure selected from alkylene, alkyl substituted alkylene, alkenylene and alkyl substituted alkenylene.

Specific embodiments are (1) wherein R is alkenyl and $R_1$ is haloalkenyl, (2) wherein R is alkenyl and $R_1$ is alkyl, (3) wherein R and $R_1$ are alkenyl, (4) wherein R and $R_1$ are alkyl, (5) wherein R is alkyl and $R_1$ is haloalkenyl, (6) wherein R is alkoxyalkyl and $R_1$ is cycloalkenyl, (7) wherein R is alkyl and $R_1$ is alkenyl, (8) wherein R is hydrogen and $R_1$ is alkoxyalkyl, (9) wherein R and $R_1$ taken together form an alkylene or alkyl substituted alkylene and (10) wherein R and $R_1$ taken together form an alkenylene or alkyl substituted alkenylene.

In general, the compounds of this invention are manufactured by reacting an appropriate amine admixed with an acid acceptor, a suitable inert solvent such as benzene or chloroform with 3,5-dimethylaryl acid chloride at reduced temperatures. The product can be separated in relatively high purity.

In order to illustrate the merits of the present invention the following examples are provided.

EXAMPLE 1

N-2-chloroallyl-N-allyl-3,5-dimethylbenzamide

A solution was formed by dissolving N-allyl-2-chloroallylamine (0.032 moles) in 40 ml. of benzene. Then, triethylamine (0.032 moles) was added thereto. This solution was then cooled to 10°C. in an ice bath. Then, 3,5-dimethylbenzoylchloride was diluted with 40 ml. of benzene and added to the amine solution. The temperature rose to about 35°C. with triethylamine hydrogen chloride separation. The next day the reaction mixture was washed two times with diluted HCl and then two times with dilute (5% solution) sodium carbonate and dried. The solvent was removed to yield 7.0 grams of product $N_D^{30}$ 1.5367.

EXAMPLE 2

N-allyl-N-isobutyl-3,5-dimethylbenzamide

The process of Example 1 was repeated in its entirety except allyl isobutylamine was used in place of the N-allyl-2-chloroallylamine. The product obtained was 6.8 grams $N_D^{30}$ 1.5130.

EXAMPLE 3

N-propyl-N-2-chloroallyl-3,5-dimethyl benzamide

The procedure in Example 1 was repeated in its entirety except N-propyl-N-2-chloroallylamine was used as the reactive amine to yield 7.2 grams of product $N_D^{30}$ 1.5274.

EXAMPLE 4

3,5-dimethylbenzoylhexamethyleneimine

A solution was formed containing hexamethyleneimine (0.032 moles) dissolved in 60 ml. of chloroform with triethylamine (0.035 moles) added thereto. This solution was cooled to 5°C in an ice bath. Then, 3,5-dimethylbenzoylchloride (0.030 moles) was diluted with 20 ml. of chloroform and added to the amine solution portion wise with mixing. An exothermic reaction occurred and the temperature rose to 38°C. The mixture was allowed to stand at room temperature overnight and was worked up by washing with two portions of 100 ml. of dilute hydrochloric acid and two portions of 100 ml. of a 5% solution of sodium carbonate to yield 6.1 grams of product $N_D^{30}$ 1.5440.

EXAMPLE 5

N-isopropoxypropyl-n-cyclohexenyl-3,5-benzamide

A solution was formed containing 4.9 grams (0.025 moles) of isopropoxypropylcyclohexylidene amine, 4.5 ml. of triethylamine in 100 ml. of benzene. Thereafter, 4.2 grams (0.025 moles) of 3,5-dimethylbenzoylchloride was added over a period of 30 seconds. The temperature rose to 35°C. After standing overnight, the mixture was washed with 100 ml. of water, then 50 ml. of saturated sodium bicarbonate solution, another 100 ml. of water, dried over magnesium sulfate and evaporated in vacuo to 6.8 grams of product $N_D^{30}$ 1.5212.

EXAMPLE 6

N-methoxyethyl-n-cyclohexenyl-3,5-dimethylbenzamide

The procedure of Example 5 was repeated in its entirety except methoxyethyl cyclohexylidene amine was used as the reactive amine to yield 7.5 grams of product $N_D^{30}$ 1.5374.

EXAMPLE 7

N-furfuryl-3,5-dimethylbenzamide

A mixture was formed containing 3.0 grams (0.03 moles) of tetrahydrofurfurylamine, 4.5 ml. triethylamine in 100 ml. benzene. Then, 3.7 ml. (0.25 moles) of 3,5-dimethylbenzylchloride was added. After standing for ½ hour, the mixture was washed with 100 ml. of water, 1 normal HCl (50 ml.), 50 ml. of saturated sodium bicarbonate, dried over magnesium sulfate and evaporated in vacuo to yield 4.4 grams of product $N_D^{30}$ 1.5366.

EXAMPLE 8

N-isopropoxypropyl-3,5-dimethylbenzamide

The procedure of Example 7 was repeated in its entirety except isopropoxypropylamine was used as the reactive amine. To yield 5.8 grams of product $N_D^{30}$ 1.5107.

The following Table is a list of compounds made in accordance with procedures of this invention.

TABLE I

Structure: 3,5-dimethylbenzamide with N-R, R₁ substituents

| Compound Number | R | R₁ | Physical Constant |
|---|---|---|---|
| 1 | —CH₂—CH=CH₂ | —CH₂—C(Cl)=CH₂ | $N_D^{30}$ 1.5367 |
| 2 | —CH₂—CH=CH₂ | —CH₂—CH(CH₃)—CH₃ | $N_D^{30}$ 1.5130 |
| 3 | —CH₂—CH=CH₂ | —(CH₂)₃—CH₃ | $N_D^{30}$ 1.5136 |
| 4 | -n-C₃H₇ | —CH₂—C(Cl)=CH₂ | $N_D^{30}$ 1.5274 |
| 5 | —CH₂—CH=CH₂ | —CH₃ | $N_D^{30}$ 1.5329 |
| 6 | —CH₂—CH=CH₂ | —C₂H₅ | $N_D^{30}$ 1.5234 |
| 7 | —CH₂CN | —CH₃ | $N_D^{30}$ 1.5345 |
| 8 | —C₂H₅ | —C₂H₅ | $N_D^{30}$ 1.5168 |
| 9 | —CH₂—CH=CH₂ | —CH₂—CH=CH₂ | $N_D^{30}$ 1.5292 |
| 10 | cyclohexyl (ring) | | m.p. 56–58°C |
| 11 | cycloheptyl (ring) | | $N_D^{30}$ 1.5440 |
| 12 | 2,5-dimethyl-cyclopentenyl (ring) | | $N_D^{30}$ 1.5342 |
| 13 | 2,6-dimethyl-cyclohexyl (ring) | | m.p. 80–84°C |
| 14 | cyclopentyl (ring) | | m.p. 50–53°C |
| 15 | —(CH₂)₃—O—CH(CH₃)₂ | cyclohexyl | $N_D^{30}$ 1.5212 |
| 16 | —CH₂—CH₂—O—CH₃ | cyclohexyl | $N_D^{30}$ 1.5374 |
| 17 | —(CH₂)₃—O—CH₃ | cyclohexyl | $N_D^{30}$ 1.5286 |
| 18 | -n-C₃H₇ | —CH₂—CH=CH₂ | $N_D^{30}$ 1.5286 |
| 19 | H | —CH₂—(furyl) | $N_D^{30}$ 1.5366 |
| 20 | H | —(CH₂)₃—O—CH(CH₃)₂ | $N_D^{30}$ 1.5107 |
| 21 | H | —CH₂—CH₂—O—CH₃ | $N_D^{30}$ 1.5297 |

TESTING PROCEDURE

Each test cage consists of a tule-covered, number 116, 16 oz. waxed paper Dixie cup with two ¾ oz. waxed paper condiment cups stapled on opposite sides of the upper, interior perimeter. One of the cups contains a sugar cube saturated with 0.8 ml. of acetone containing a specific concentration of the test repellent and allowed to dry. The second condiment cup contains a water-saturated cotton plug. After each cube has been treated and allowed to dry, it is carefully weighed and placed in the test cage. One hundred house flies of mixed sexes are then placed in the cages and all of the cages are placed on a 1½ r.p.m. turntable. This procedure keeps the flies in random distribution within the cage and eliminates their gathering on the cage walls due to a phototropic response to outside light sources. Such gathering was found to give a false appearance of repellency by the sugar cube. Seventy-two hours after treatment, the flies in each cage are anesthesized with $CO_2$, the cube is removed and reweighed and the percentage weight loss of the cube (due to consumption by the flies) is recorded. The cubes with the least weight loss are considered to be the most repellent to the flies. A "repellency ratio" is calculated by dividing the percentage weight loss of the treated cubes by the percentage weight loss of the acetone treated control cubes. The value of this ratio is then inversely proportional to the repellency of the test compound and is listed in the following table.

| Compound Number | Repellency 1.0% | Ratio 0.1% |
|---|---|---|
| 1 | 0.34 | 0.77 |
| 2 | 0.16 | 0.69 |
| 3 | 0.20 | 0.69 |
| 4 | 0.34 | 0.63 |
| 5 | 0.40 | 0.95 |
| 6 | 0.25 | 0.95 |
| 7 | 0.87 | 1.1 |
| 8 | 0.39 | 0.97 |
| 9 | 0.42 | 0.79 |
| 10 | 0.52 | 0.85 |
| 11 | 0.51 | 0.97 |
| 12 | 0.46 | 0.89 |
| 13 | 0.81 | 0.94 |
| 14 | 0.56 | 0.92 |
| 15 | 0.23 | 0.49 |
| 16 | 0.40 | 0.64 |
| 17 | 0.22 | 0.58 |
| 18 | 0.31 | 0.82 |
| 19 | 0.89 | 0.96 |
| 20 | 0.40 | 0.73 |
| 21 | 0.92 | 1.02 |

The compounds of the present invention can be used in any convenient form. Thus, the compounds can be made into emulsifiable liquids, emulsifiable concentrates, liquid, wettable powder, powders, granular or any other convenient form.

In the above description of the compounds, the following embodiments are intended for the various substituent groups: alkyl includes, unless otherwise provided for, those members which contain from 1 to 8 carbon atoms, inclusive, in both straight and branched chain configurations; alkenyl and cycloalkenyl include unless otherwise provided for, those members which contain at least one olefinic double bond and contain from 2 to 6 carbon atoms, inclusive, in both straight and branched chain configurations; and alkylene and alkenylene includes, unless otherwise provided for, those members which contain from 2 to 6 carbon atoms.

What is claimed is:
1. A compound having the formula:

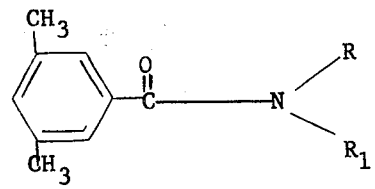

wherein R is selected from the group consisting of hydrogen and alkoxyalkyl; $R_1$ is selected from the group consisting of cycloalkenyl and alkoxyalkyl.

2. The compound of claim 1 wherein R is

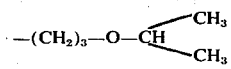

and

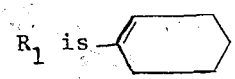

3. The compound of claim 1 wherein R is —CH$_2$—CH$_2$—O—CH$_3$ and

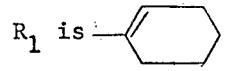

4. The compound of claim 1 wherein R is —(CH$_2$)$_3$—O—CH$_3$ and

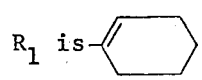

5. The compound of claim 1 wherein R is H and $R_1$ is

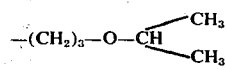

6. The compound of claim 1 wherein R is H and $R_1$ is —CH$_2$—CH$_2$—O—CH$_3$.

* * * * *